United States Patent [19]

Mannheimer et al.

[11] Patent Number: 5,099,842
[45] Date of Patent: Mar. 31, 1992

[54] PERINATAL PULSE OXIMETRY PROBE

[75] Inventors: Paul D. Mannheimer, Belmont; Carl Ritson, San Jose, both of Calif.

[73] Assignee: Nellcor Incorporated, Hayward, Calif.

[21] Appl. No.: 504,235

[22] Filed: Apr. 4, 1990

Related U.S. Application Data

[63] Continuation-in-part of Ser. No. 264,196, Oct. 28, 1988, Pat. No. 4,938,218.

[51] Int. Cl.⁵ .............................................. A61B 5/00
[52] U.S. Cl. ................................................. 128/633
[58] Field of Search .......................... 128/633-634, 128/643, 664-666; 356/40, 41

[56] References Cited

U.S. PATENT DOCUMENTS

| 3,505,993 | 4/1970 | Lewes et al. ..................... | 128/643 |
| 4,537,197 | 8/1985 | Hulka ................................ | 128/634 |
| 4,859,057 | 8/1989 | Taylor et al. . | |
| 4,880,304 | 11/1989 | Jaeb et al. ....................... | 128/633 |

FOREIGN PATENT DOCUMENTS

| 0135840 | 4/1985 | European Pat. Off. ............ | 128/633 |
| 0285307 | 10/1988 | European Pat. Off. . | |
| 0001293 | 2/1990 | PCT Int'l Appl. ................. | 128/634 |

Primary Examiner—Ruth S. Smith
Attorney, Agent, or Firm—Townsend and Townsend

[57] ABSTRACT

A fetal pulse oximetry probe has clusters of light-transmissive bumps over the light source and the light detector on the surface of the probe. The probe is usually attached to the fetus' head. The clusters part the fetal hair and penetrate other light-attenuating organic materials on the head. The clusters thus transmit a more intense light signal. To reduce the amount of signal shunting between them, the clusters also may be separated by additional opaque (light-shielding) bumps.

12 Claims, 4 Drawing Sheets

PERINATAL PULSE OXIMETRY PROBE

PRIOR APPLICATION

This application is a continuation-in-part of U.S. Pat. No. 4,938,218 entitled "Improved Perinatal Pulse Oximetry Probe."

BACKGROUND OF THE INVENTION

The present invention relates to transflectance-type fetal pulse oximetry probes. "Transflectance" probes attach to a single physiological surface. Their light source and detector need not lie on opposite sides of the pulsatile tissue. "Transmission" probes, by contrast, monitor signals across pulsatile tissue, for example signals passing from the dorsal to the volar surface of a finger. The invention relates to improvements for transflectance probes, especially to enhance the light signal in the presence of fetal hair or other light-attenuating materials when the probe is attached to the head.

Application Ser. No. 264,196, here incorporated by reference, describes various embodiments of an improved perinatal pulse oximetry probe. The function of the probe and the nature of pulse oximetry are discussed in that application and will not be repeated here. The application particularly refers to "curved surface portions" through which the optical signals pass. When brought into contact with the fetal tissue, these curved portions create a dimple in the tissue surface.

The dimple helps prevent light from shunting between the source and the detector without passing through blood-perfused tissue. It also improves the contact between the probe and the fetal tissue. Nonetheless the oximetry readings, if made on the head, may be inaccurate or inconsistent due to low light levels, i.e., poor signal-to-noise ratio. The optical signal levels may be attenuated by intra-uterine materials like blood, dead cells, mucous, vernix caseosa, or fetal hair. These materials and fetal hair collectively will be referred to as "substances."

SUMMARY OF THE INVENTION

The purpose of the present invention is to improve the accuracy and consistency of the readings, especially in the presence of substances, by increasing the optical signal levels.

Various methods may be used to increase signal levels by intensifying the emitted light from the probe and increasing the sensitivity of the detector. However, substances like hair may significantly lessen the amount of light passing between the probe and the skin and consequently decrease the signal-to-noise ratio.

To overcome this problem, the invention reduces the amount of substances between the probe and the fetal tissue. In the probe of the prior application, the curved surface portions or bumps improve the signal. The apex of the bump pushes aside the substances and comes to rest on the scalp (or close to it). The clusters in the present invention more effectively penetrate the substances on the head.

The clusters "scrub" aside the substances better than does the single bump of the prior invention. Clusters also are more effective when used over larger surface areas of the source and detector. A single bump, if too flat, would not effectively part the fetal hair and penetrate the other light-attenuating materials. But if too high, a single bump would hold the probe too far above the fetal tissue.

The present invention therefore uses clusters of bumps over the source, the detector, or both. The bumps in the clusters are sufficiently pointed to penetrate the substances. The action of these bumps is much like combing. Like the teeth of a comb, the bumps penetrate a wad of hair or other material. When the probe, biased toward the head, is slid back and forth, the "comb" also moves aside substances caught underneath its "teeth" (i.e., the bumps). As the probe slides back and forth the substances are forced away from the apex of the bumps. The spaces between the bumps receive the substances that are pushed aside.

It is an object of the invention to provide a cluster of bumps on a fetal oximetry probe to part the fetal hair and penetrate other light-attenuating materials to provide a relatively unobstructed light path between the probe and the skin, thus raising the optical signal level.

BRIEF DESCRIPTION OF THE DRAWINGS

In all drawings, like parts are designated by like reference numbers.

DETAILED DESCRIPTION OF THE EMBODIMENTS

Figure 1A:
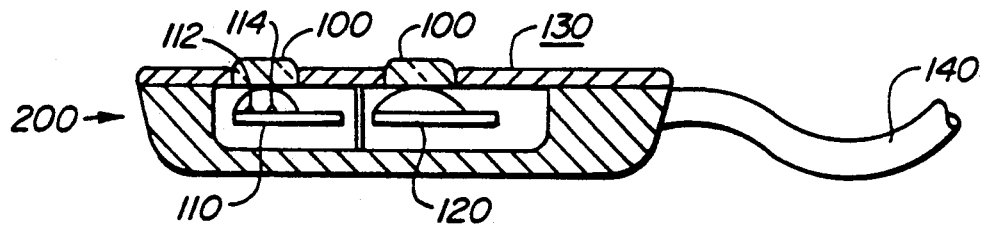
FIG. 1(a) is a cross-sectional view of an embodiment of the probe of the present invention.

Several embodiments of the present invention are described and shown in the drawings.

Figure 1B:
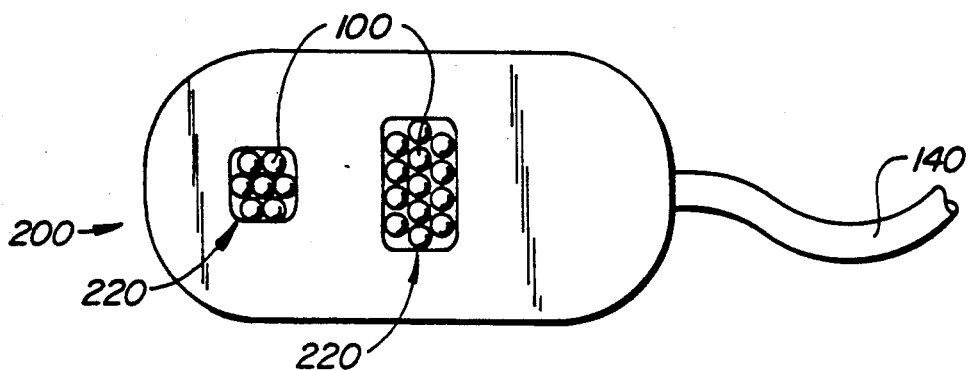
FIG. 1(b) is a top view of the probe of FIG. 1(a).

FIG. 1(a) shows a perinatal pulse oximetry probe 200 that includes light source 110, detector 120, and cord 140. The probe can be made of acrylonitrile-co-butadiene-co-styrene (ABS) plastic or any bio-compatible flexible or inflexible material. Source 110 and detector 120 are covered by light-transmissive bumps 100. Opaque surface 130 covers the probe 200. FIG. 1(b) shows the clusters 220 of bumps 100. Cord 140 connects probe 200 to a power source.

Figure 2A:
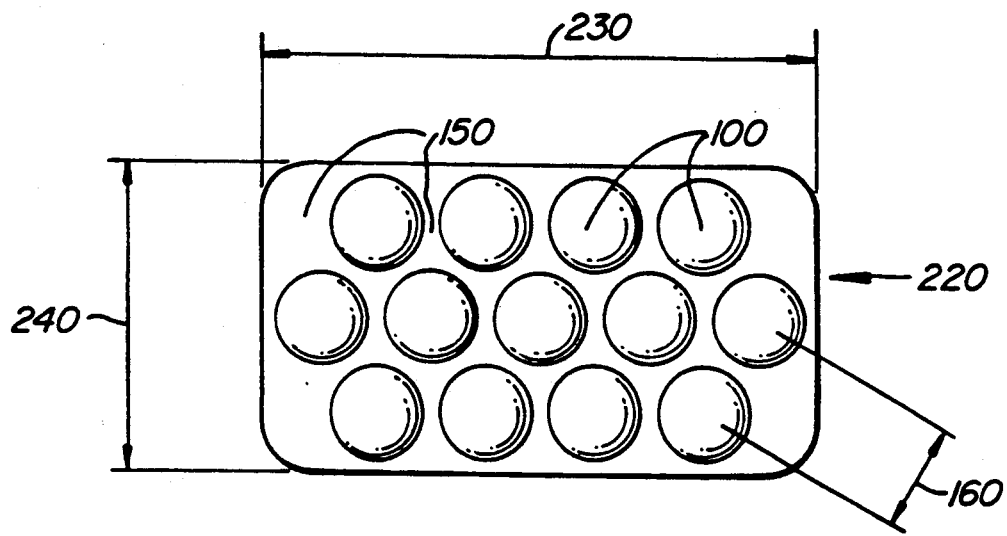
FIG. 2(a) is a top view of a cluster of bumps.
Figure 2B:
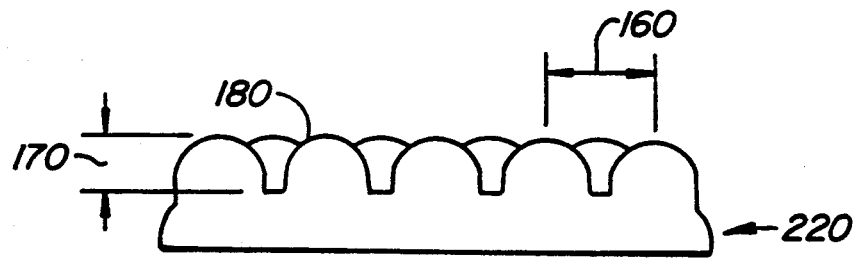
FIG. 2(b) is cross-sectional view of a cluster of bumps.

FIGS. 2a-b is an enlarged view of clusters 220 of bumps 100. These clusters cover source 110 and detector 120 of FIGS. 1a-b. The bumps 100 are separated by spaces 150. The spaces are non-raised areas of the probe's surface.

In FIG. 2(a) the distance 160 is identified as measured between the centers of any two adjacent bumps 100. In one embodiment this distance is 0.053 inches. Measurements 230 and 240 are the length and width, respectively, of the clusters. The size and shape of the source and detector can vary. In the preferred embodiment the source is covered by seven bumps and is 0.15 inches×0.17 inches; the detector is covered by thirteen bumps and is 0.165 inches×0.30 inches.

As is conventional in pulse oximetry, source 110 provides light of two different wavelengths (red and infrared). To further intensify the signal, this particular embodiment uses a light source having three light-emitting diodes or "LEDs" (two red LEDs 112, one infrared LED 114) that each generate the necessary red and infra-red wavelengths (660 and 900 nanometers, respectively).

The red wavelength especially is attenuated by darkly pigmented hair. The thickness of the hair also attenuates the signal. Such interference can cause too great a variation in the ratio of red to infra-red signals. The applicants have observed red-to-infrared transmission ratios of 1:4 for lightly pigmented hair, and as little as 1:150 for darker pigments. Using clusters of bumps to provide a relatively less obstructed path makes the ratio more consistent.

In FIG. 2(b) measurement 170 is the height of each bump 100 (its radius, if hemispherical). One embodiment has bumps with a radius of curvature of 0.024 inches and an overall height of 0.033 inches. Curve 180 is the arc, or radius of curvature, of each bump 100. The bumps can be non-hemispheric, for example parabolic, conical, or domed. The bumps are shown as uniform, but their individual dimensions and shapes may vary. Bumps with smaller aspect ratios (width to height) more effectively push the hair aside and penetrate the light-attenuating materials than do bumps with larger aspect ratios.

As shown in FIG. 2(a), the size and placement of light-transmissive bumps 100 in cluster 220 allow for spaces between bumps 100 to receive the displaced substances.

An alternative embodiment involves the use of spherical bumps that are undercut below opaque cover 130. Most of the sphere would protrude above the surface of the probe. This arrangement would better trap the substances beneath the "shelf" formed by each sphere's equator.

The light-transmissive bumps can be constructed in various ways. In the preferred embodiment, the bump cluster is cast in transparent UV-curable epoxy (Hysol UV6000, for example) in an aluminum or Teflon mold. The same epoxy is then used to bond the cluster to the source and detector. Other methods, including injection molding and transfer molding directly onto the optoelectronic substrate, are possible as well.

Figure 3A:
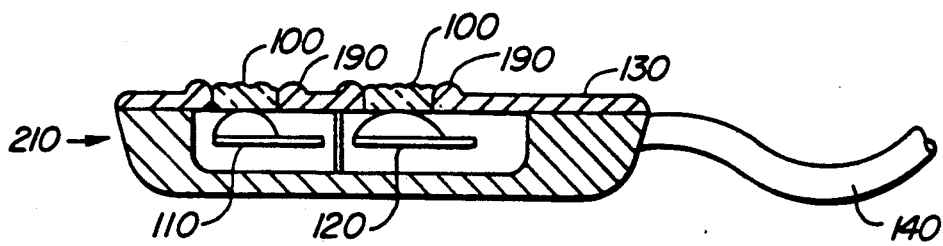
FIG. 3(a) is a cross-sectional view of an alternative embodiment of the probe of the present invention, showing opaque bumps.
Figure 3B:
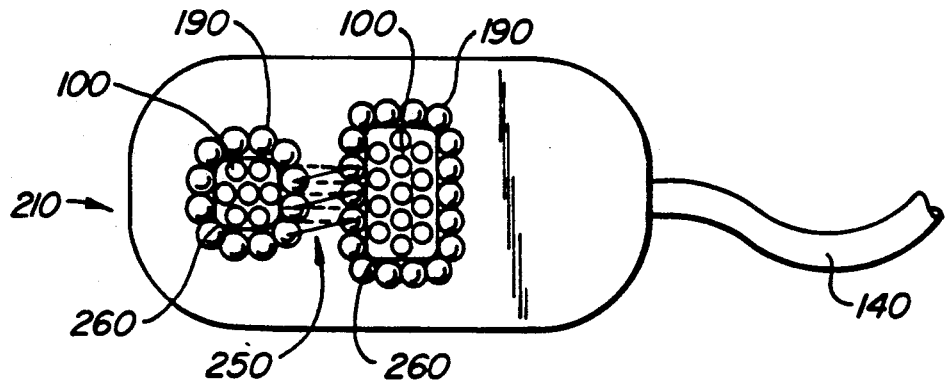
FIG. 3(b) is a top view of the probe of FIG. 3(a), showing opaque bumps.
Figure 1C:
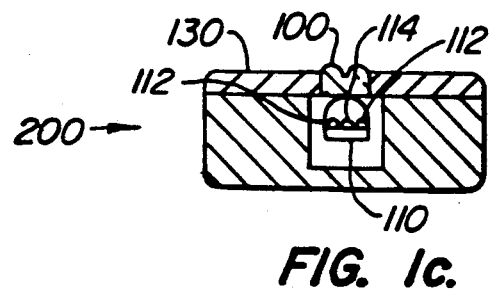
FIG. 1(c) is a second cross-sectional view of the embodiment of FIGS. 1(a) and 1(b).

FIG. 3(a) shows a perinatal pulse oximetry probe 210 that includes light source 110, detector 120, and cord 140. Light-transmissive bumps 100 are bordered by opaque bumps 190. The opaque bumps may be of one piece with opaque surface 130, as shown, or separate pieces attached to surface 130. The opaque bumps may be shaped and sized differently from the light-transmissive bumps. FIG. 3(b), a top view, shows light-transmissive bumps 100 encircled by opaque bumps 190.

Alternatively, opaque bumps 190 can be placed between light-transmissive bumps 100 without enclosing them. In one embodiment, the two facing rows of opaque bumps are staggered such that lines 250 drawn through their centers are diagonal to the edges 260 of the source and detector.

The opaque bumps reduce the amount of light shunting between the source and detector, that is, diffusing sideways and bypassing the blood-perfused fetal tissue. Shunting distorts the calibration of the pulse oximetry measurements.

Another alternative embodiment would use optical fibers, which pass light through a defined core. Many short fibers could be arranged vertically on the surface of the probe, with small spaces between them. The spaces would receive the substances pushed aside by the tips of the fibers, the equivalent of the bumps in the preferred embodiment. These "light combs" would have the advantage of being both transmitter and barrier: they would pass the light signal in a confined path and thus reduce shunting. In one variation of this embodiment the optical fibers would extend outside the patient's body to an external light source and detector, as in the prior application.

Figure 4:
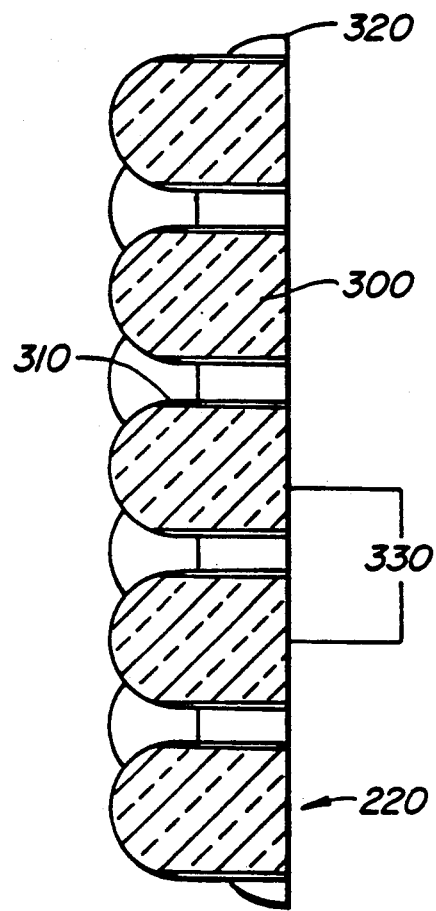
FIG. 4 is a cross-sectional view of an alternative embodiment of the cluster of bumps, using optical fibers.

FIG. 4 shows that alternative embodiment, with cluster 200 comprised of optical fibers 330. These fibers consist of an optical core 300 and cladding 310. The fibers are surrounded by an opaque matrix 320 which further reduces shunting.

The probe can be attached to the fetal tissue by any practical means including suction, compression, adhesives, or clips.

Figure 5A:
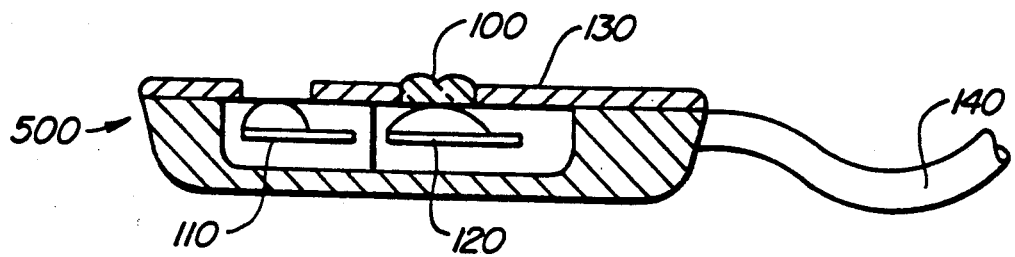
FIG. 5(a) is a cross-sectional view of an alternative embodiment of the probe of the present invention.
Figure 5B:
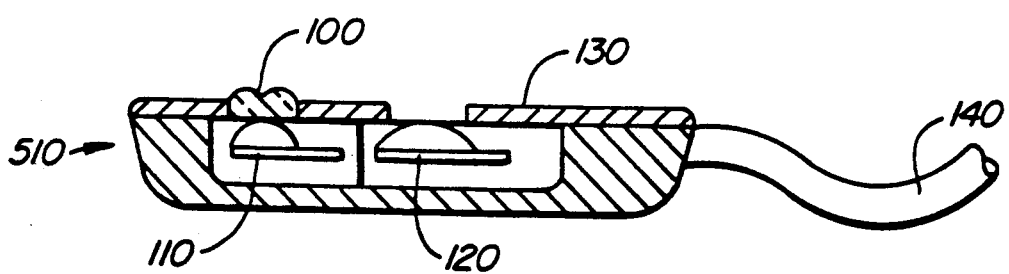
FIG. 5(b) is a cross-sectional view of another alternative embodiment of the probe of the present invention.

FIGS. 5a-b show another alternative embodiment where either only the light source 110 or the detector 120 is covered by light transmissive bumps 100. FIG. 5a shows the probe 500 with only detector 120 having light transmissive bumps 100 as a cover, while FIG. 5b shows the probe 510 with only light source 110 having light transmissive bumps 100 as a cover.

The invention, an improved perinatal pulse oximetry probe as illustrated above, is defined by the claims that follow.

We claim:

1. A transflectance-type pulse oximetry probe comprising:
   a light source and a light detector mounted within a probe, the light source operating at a plurality of wavelengths;
   means for transmitting electrical signals to and from the probe;
   and a cluster of light-transmissive bumps covering the light source and arranged so that light at each wavelength may be transmitted through all of the bumps.

2. The probe of claim 1 wherein the light-transmissive bumps have rounded surfaces.

3. The probe of claim 1 wherein the light-transmissive bumps are sufficiently high to penetrate light-attenuating materials.

4. The probe of claim 1 wherein the light-transmissive bumps have an aspect ratio sufficient to penetrate light-attenuating materials.

5. A transflectance-type pulse oximetry probe comprising:
   a light source and a light detector mounted within a probe;
   means for transmitting electrical signals to and from the probe; and
   a cluster of light-transmissive bumps covering the light detector.

6. A transflectance-type pulse oximetry probe comprising:
   a light source and a light detector mounted within a probe;
   means for transmitting electrical signals to and from the probe;

a first cluster of light-transmissive bumps covering the light source; and a second cluster of light-transmissive bumps covering the light detector.

7. The probe of claim 6 wherein the surface of the probe has one or more opaque bumps between the clusters.

8. A transflectance-type pulse oximetry probe comprising:

a light source and a light detector mounted within a probe;

means for transmitting electrical signals to and from the probe;

a cluster of light-transmissive bumps covering one or the other of the light source and light detector; and a plurality of opaque bumps surrounding the cluster of light-transmissive bumps.

9. A transflectance-type pulse oximetry probe comprising:

a light source and a light detector mounted within a probe;

means for transmitting electrical signals to and from the probe; and a cluster of light-transmissive bumps covering one or the other of the light source and light detector, and wherein the cluster of light-transmissive bumps comprises optical fibers.

10. The probe of claim 9 wherein the optical fibers are surrounded by opaque material.

11. A method for displacing hair and other light-attenuating materials from the paths of optical signals in a transflectance-type pulse oximetry probe, the probe comprising a light source and a light detector mounted within the probe and further comprising means for transmitting electrical signals to and from the probe, the method comprising the steps of (a) providing a cluster of light-transmissive bumps covering one or the other of the light source and the light detector; and (b) positioning the probe by sliding it back and forth over the tissue such that the hair and other light-attenuating materials are displaced between the bumps.

12. The method of claim 11 wherein the cluster of light-transmissive bumps covers the light source, and wherein the method further comprises the steps of providing a second cluster of light-transmissive bumps covering the light detector, whereby the probe is positioned by sliding it back and forth over the tissue such that the hair and other light-attenuating materials are displaced between the bumps of the second cluster.

* * * * *